(12) United States Patent
Lonien et al.

(10) Patent No.: US 8,696,624 B2
(45) Date of Patent: Apr. 15, 2014

(54) TAMPER-PROOF INJECTOR OR APPLICATOR FOR DISPENSING A LIQUID OR PASTY DRUG

(75) Inventors: Birgit Lonien, Dudeldorf (DE); Sascha Mohs, Dudeldorf (DE)

(73) Assignee: elm-Plastic GmbH, Dudeldorf (DE)

(*) Notice: Subject to any disclaimer, the term of this patent is extended or adjusted under 35 U.S.C. 154(b) by 1001 days.

(21) Appl. No.: 11/821,038

(22) Filed: Jun. 21, 2007

(65) Prior Publication Data

US 2008/0077086 A1 Mar. 27, 2008

(30) Foreign Application Priority Data

Jun. 22, 2006 (DE) .......................... 10 2006 028678
Sep. 13, 2006 (DE) .......................... 10 2006 043033

(51) Int. Cl.
*A61M 5/00* (2006.01)
*A61M 3/00* (2006.01)

(52) U.S. Cl.
USPC ........................... 604/110; 604/111; 604/195

(58) Field of Classification Search
USPC ....................................................... 604/110
See application file for complete search history.

(56) References Cited

U.S. PATENT DOCUMENTS

| | | | |
|---|---|---|---|
| 4,961,728 A | 10/1990 | Kosinski | |
| 5,037,393 A | 8/1991 | Ellgass | |
| 5,090,962 A | 2/1992 | Landry, Jr. et al. | |
| 5,127,906 A | 7/1992 | Landry, Jr. et al. | |
| 5,195,985 A * | 3/1993 | Hall | 604/195 |
| 5,269,760 A * | 12/1993 | Bina | 604/110 |
| 7,090,656 B1 * | 8/2006 | Botich et al. | 604/110 |
| 2004/0064095 A1 * | 4/2004 | Vitello | 604/111 |
| 2004/0116858 A1 | 6/2004 | Heinz et al. | |
| 2007/0270743 A1 * | 11/2007 | Ackerman | 604/110 |

FOREIGN PATENT DOCUMENTS

| | | |
|---|---|---|
| DE | 3879678 | 9/1993 |
| DE | 68909905 | 4/1994 |
| DE | 69015245 | 8/1995 |
| DE | 20311109 | 10/2003 |
| DE | 10247965 | 5/2004 |
| EP | 1477128 | 11/2004 |
| WO | 03/057289 | 7/2003 |

* cited by examiner

*Primary Examiner* — Nicholas Lucchesi
*Assistant Examiner* — Ian Holloway
(74) *Attorney, Agent, or Firm* — Dilworth & Barrese, LLP.

(57) ABSTRACT

An injector or applicator is used for dispensing a liquid or pasty drug. It comprises an injector body (1), a piston body (2) and a closing cap (3). The closing cap (3) has a cap portion and a connecting portion. The cap portion is used for closing the opening of the injector or applicator. The connecting portion is used for connecting the closing cap (3) with the injector or applicator. The cap portion and the connecting portion are releasably connected by a tear edge. To create an improved tamper-proof feature, the housing portion (1) has an undercut, and the piston body (2) has a protrusion (FIG. 6).

16 Claims, 2 Drawing Sheets

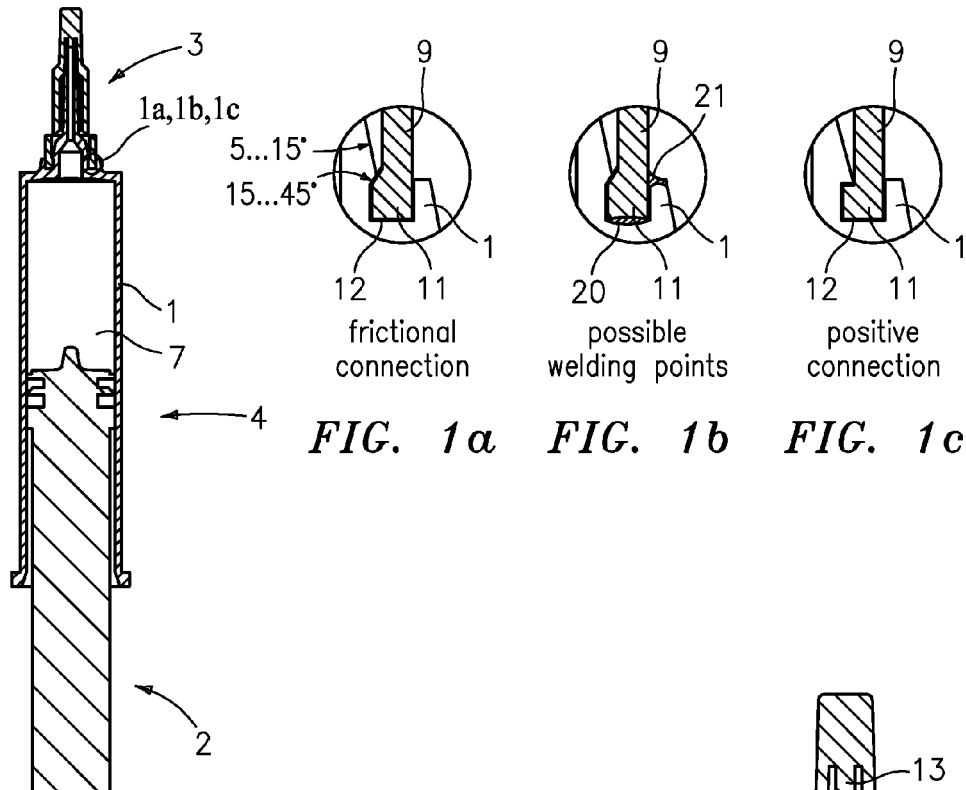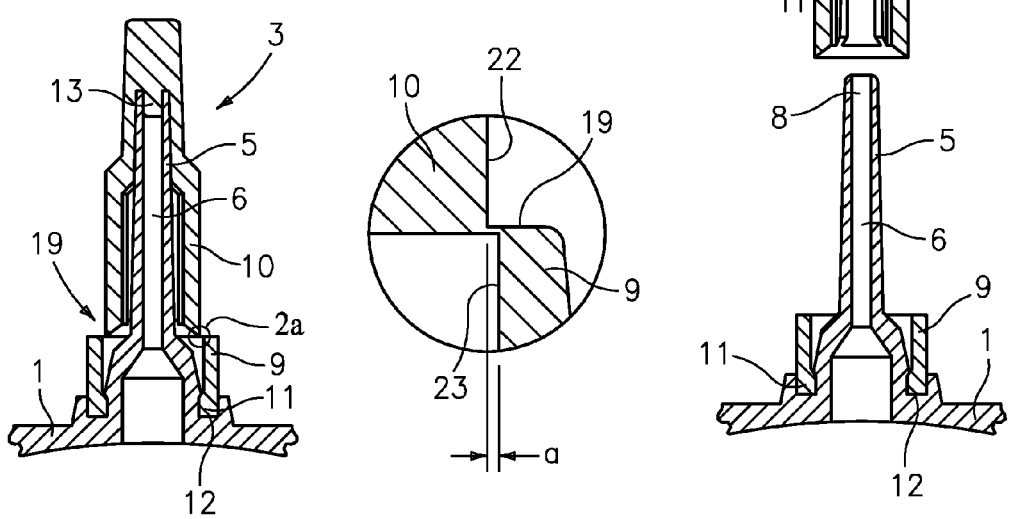

TAMPER-PROOF INJECTOR OR APPLICATOR FOR DISPENSING A LIQUID OR PASTY DRUG

BACKGROUND OF THE INVENTION

This invention relates to a tamper-proof injector or applicator for dispensing a liquid or pasty drug according to the generic part of claim 1. The injector or applicator is used in particular for dispensing a drug for the medical treatment of an animal, in particular for the medical treatment of the udder of an animal. In addition, the invention can be applied to any known form of administration (oral, nasal, etc.).

SUMMARY OF THE INVENTION

An injector according to the generic part of claim 1 is known from EP 1 477 128 A1. The injector includes a housing portion, a piston body and a closing cap. The closing cap comprises a cap portion for closing the opening of the injector and a connecting portion for connecting the closing cap with the injector. The cap portion and the connecting portion are releasably connected by a tear edge. This should create a tamper-proof feature.

However, the injector according to EP 1 477 128 A1 merely prevents a manipulation in the vicinity of the cap. Manipulations in the vicinity of the piston are not excluded.

Proceeding therefrom, it is the object underlying the invention to propose an injector or applicator as mentioned above with an improved tamper-proof feature.

In accordance with the invention, this object is solved by the features herein. The housing portion has an undercut. The piston body has a protrusion. The undercut and the protrusion are adjusted to each other such that the piston body or a part thereof cannot be withdrawn from the housing portion. The piston body or a part thereof are retained at the undercut when trying to withdraw the same from the housing portion. In accordance with the invention, the piston body thus is secured against withdrawal from the housing portion. An exchange or manipulation of the liquid or paste present in the housing portion, which requires a complete withdrawal of the piston body from the housing portion, is not possible. This can also prevent manipulations in the vicinity of the piston. The invention creates an improved tamper-proof feature for an injector or applicator for dispensing a liquid or pasty drug. The injector or applicator of the invention is designed to be tamper-proof or tamper-evident.

Advantageous developments are also described herein.

The housing portion can include one or more lamellae and/or one or more hooks. The lamellae and/or hooks are shaped such that they form an undercut and prevent withdrawal of the piston body from the housing portion.

The piston body can be made of one piece. For this purpose, the piston body can be formed integrally. It is, however, also possible to compose the piston body of two or more individual parts, these parts being non-releasably connected with each other. When the plunger and the piston are made of one piece, or when the plunger and the piston are made of two pieces, but are so firmly connected with each other that they cannot be separated from each other, it is achieved by means of this locking or undercut or by means of the lamellae or hooks that the entire piston body cannot be withdrawn from the housing portion.

In accordance with a further advantageous development, the piston body comprises a plunger and a piston which is releasably connected with the plunger. In this case, the protrusion of the piston body is formed by the piston. When the piston body is withdrawn from the housing portion, the piston abuts against the undercut of the housing portion. If then an attempt is made to withdraw the piston body from the housing portion by force, the piston gets stuck at the undercut. The plunger and the piston are connected with each other such that in this case the piston is separated from the plunger, so that the plunger can completely be withdrawn from the housing portion, but the piston remains in the housing portion, where it forms a tamper-proof feature and prevents a manipulation of the liquid or pasty drug present in the piston body.

When the piston body comprises a plunger and a piston, which are releasably connected with each other, the plunger and the piston can be made of one piece or of two pieces. In particular, the plunger and the piston can be connected with each other by a predetermined breaking point. Instead of a predetermined breaking point or in addition to the same, the plunger and the piston can be connected with each other by a sealing tape.

Advantageously, the connecting portion includes a clamping portion. The connecting portion thereby can be clamped to the injector or applicator.

Preferably, the connecting portion or clamping portion has a bead. The bead preferably is shaped such that it engages behind a corresponding cavity provided in the injector or applicator, in particular behind a groove.

In accordance with a further advantageous development, the connecting portion is pressed into the injector or applicator. In particular, the connecting portion can be frictionally connected with the injector or applicator. Thereby, it can be ensured in a simple way that the connecting portion remains connected with the injector or applicator when the cap portion is detached or torn off.

In accordance with a further advantageous development, the connecting portion is welded to the injector or applicator.

A further advantageous development is characterized in that the connecting portion is positively connected with the injector or applicator.

The tear edge, which connects the cap portion and the connecting portion, preferably extends in radial direction.

Advantageously, the cap portion has a sealing pin. The sealing pin preferably is shaped such that it engages in the opening of the tip of the housing portion and sealingly closes the same, when the closing cap is connected with the injector or applicator and the cap portion is not yet detached from the connecting portion.

BRIEF DESCRIPTION OF THE DRAWINGS

One embodiment of the invention will subsequently be explained in detail with reference to the attached drawing, in which:

FIG. 1 shows an injector with attached closing cap in a sectional side view,

FIGS. 1a, b, c, show enlarged partial views of FIG. 1,

FIG. 2 shows the upper end of the injector and the closing cap in an enlarged representation, FIG. 2a shows an enlarged partial view of FIG. 2, FIG. 3 shows the closing cap upon detachment of the cap portion.

DESCRIPTION OF THE PREFERRED EMBODIMENTS

Figure 7:
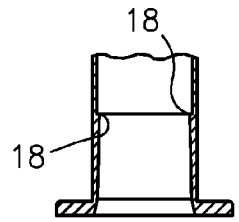
FIG. 7 shows the rear part of the housing portion in an enlarged representation.

The injector 4 shown in the drawing, which can also be referred to as injection syringe, comprises a housing portion 1 and a piston body 2 which is longitudinally movable therein. At the front end of the housing portion 1, a tip 5 is provided, which is integrally formed with the housing portion 1. Inside the tip 5, a channel 6 is located, which is connected with the cavity 7 between the piston body 2 and the housing portion 1 and which opens into an opening 8 at the outer end of the tip 5.

As shown in particular in FIGS. 1, 2 and 3, the closing cap 3 comprises a connecting portion 9 and a cap portion 10. At its lower end, the connecting portion 9 has a circumferential bead 11, which engages behind a corresponding groove 12 in the housing portion 1. The groove 12 is provided in the vicinity of the front end of the housing portion 1 on the outside thereof. It extends around the tip 5 in its base portion.

In the embodiment shown in FIG. 1a, the bead 11 is frictionally connected with the groove 12. In its cross-section, the groove 12 is closed over a region of more than 180°, so that the bead 11 is retained therein. The cross-section of the groove 12 extends substantially U-shaped. The radially outer leg of the U-shaped profile of the groove 12 linearly extends in upward direction. In its upper end portion, the radially inner leg includes a bevel which extends towards the middle of the groove 12. The angle of this bevel is 15 to 45°. The adjoining region of the connecting portion 9 extends at an angle of 5 to 15° away from the groove 12. The bead 11 extends complementary to the groove 12. It is introduced into the groove 12 and clamped to or pressed into the groove, whereby the connecting portion 9 is firmly fixed on the housing portion 1.

In the variant shown in FIG. 1b, the bead 11 is welded to the connecting portion 9. The first weld 20 is located at the base of the groove 12. The second weld 21 is located at the upper end of the outer leg of the U-shaped profile of the groove 12. It is possible to provide both welds 20, 21 or only one thereof. Moreover, the shapes of the bead 11 and of the groove 12 in the embodiment of FIG. 1b correspond to the shape as shown in FIG. 1a. The welds 20 and/or 21 can be provided in addition to the frictional connection as shown in FIG. 1a. However, it is also possible that the connecting forces are effected mostly or exclusively by one or both welds 20, 21. Furthermore, an undercut of the bead 11 in the groove 12 can be omitted in the case of one or more welds 20, 21.

In the embodiment as shown in FIG. 1c, the bead 11 is positively connected with the groove 12. Here, the angle of the bevel is not 15 to 45°, as in FIG. 1a, but 90°.

The cap portion 10 has a sealing pin 13, which is located inside the upper terminal region of the cap portion 10 and is directed downwards. When the closing cap 3 is connected with the housing portion 1, the sealing pin 13 engages in the opening 8 of the tip 5 of the housing portion 1, as can be taken in particular from FIG. 2. The opening 8 is sealingly closed by the sealing pin 13.

The connecting portion 9 and the cap portion 10 are connected with each other by a tear edge 19. The tear edge is formed by a circumferential ring portion of small cross-section. It connects the upper terminal region of the connecting portion 9 with the lower terminal region of the cap portion 10. Connecting portion 9, cap portion 10 and tear edge 19 are formed integrally. As can be taken in particular from FIG. 2a, the tear edge 19 extends in radial direction. In the profile representation shown in FIG. 3, the outer profile edge 22 of the cap portion 10 radially extends further on the inside than the inner edge 23 of the connecting portion 9. The resulting offset a is bridged by the horizontally extending tear edge 19. The limits of the tear edge 19, which are horizontal as seen in profile, extend in parallel. The tear edge 19 constitutes a narrow web. As compared to the tear edge according to EP 1 477 128 A1, it has a simpler design saving more material.

When the injector should be used for dispensing the liquid or paste present in the cavity 7, the cap portion 10 must be removed. This is effected in that the cap portion 10 is torn off. In doing so, the cap portion 10 is detached from the connecting portion 9 in the vicinity of the tear edge 19. The cap portion 10 can be removed in upward direction, as shown in FIG. 3, so that the tip 5 is exposed. Since the bead 11 is clamped or pressed into the groove 12, the connecting portion 9 remains connected with the housing portion 1. As a result, it is impossible to insert a further, undamaged closing cap 3 into the groove 12 of the housing portion 1. The connecting portion 9, which remains firmly connected with the housing portion 1, thus forms a tamper-proof feature.

Figure 5:
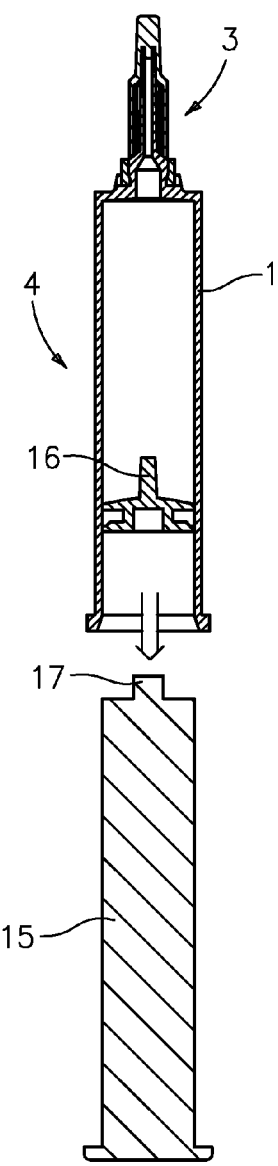
FIG. 5 shows the injector with a piston body, which comprises a plunger and a piston and is partly withdrawn from the housing portion.
Figure 6:
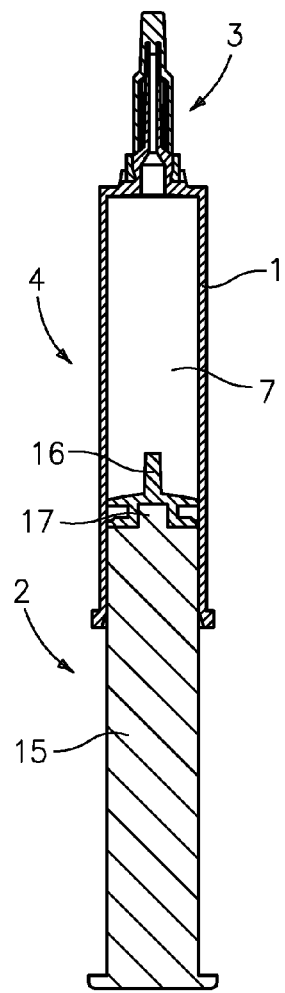
FIG. 6 shows the injector of FIG. 5 with fully withdrawn plunger.

In the embodiment shown in FIGS. 5 and 6, the piston body 2 consists of a plunger 15, which protrudes from the housing portion 1 on the rear, and of a piston 16, which faces the front part of the housing portion 1. The cavity 7 is enclosed by the housing portion 1 and by the front end face of the piston 16. Plunger 15 and piston 16 are connected with each other by a slight frictional connection. For this purpose, the plunger 15 has an elevation 17 at its front end, which engages in a corresponding depression on the back of the piston 16, where the plunger 15 and the piston 16 are clamped to each other.

In the vicinity of its rear end, the housing portion 1 has an undercut 18. The undercut 18 is formed by a step facing to the inside. This step can be formed to be circumferential. However, a plurality of steps can also be distributed around the periphery. The inside diameter of the housing portion 1 or the distance of opposed steps is smaller in the rear part of the housing portion 1 than in the part located further to the front. Furthermore, this diameter or these distances is/are adjusted to the piston 16 such that this piston 16 can be moved into the housing portion 1, but can no longer be moved out of the housing portion 1. When the piston body 2 is withdrawn from the housing portion 1, the piston 16 is retained by the undercut 18. When pulled further to the rear, the plunger 15 is detached from the piston 16, as shown in FIG. 5. In this position, the piston 16 forms a tamper-proof feature, which prevents that the liquid or paste present in the cavity 7 can be manipulated or be replaced by some other liquid or paste.

Instead of the undercut 18, one or more lamellae and/or hooks can be provided. These parts must also be adjusted to the piston 16 such that it is prevented by these parts from moving out of the housing portion 1.

It would also be possible to connect the plunger 15 and the piston 16 by a sealing tape or a similar component, which will tear when trying to withdraw the piston 16 from the housing portion 1. The sealing tape can be produced when injection molding the piston body 2.

A further possibility consists in integrally forming the plunger 15 and the piston 16 and connecting them with each other by a predetermined breaking point.

Figure 4:
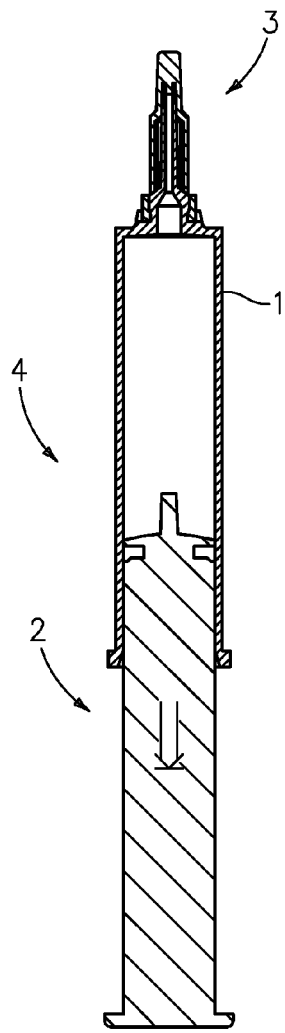
FIG. 4 shows the injector with a one-piece piston body, which is partly withdrawn from the housing portion.

In the embodiment shown in FIG. 4, the piston body 2 is made of one piece. For this purpose, the plunger 15 and the piston 16 can be formed integrally. However, the plunger 15 and the piston 16 can also be made of two pieces and be non-releasably connected with each other. In both cases, the entire piston body 2 consisting of plunger 15 and piston 16 would be prevented from being withdrawn from the housing portion 1 by the undercut 18 or a similar component.

The Figures of the drawing show a housing portion 1 and a piston body 2 of circular cross-section. However, other cross-sectional shapes are also possible, such as a cross shape or some other shape.

Another locking possibility consists in providing an indentation or bulge in the plunger 15, which cooperates with the undercut or a similar part of the housing portion 1 such that withdrawing the plunger 15 from the housing portion 1 no longer is possible.

The invention creates a tamper-proof feature for a pre-filled injector or applicator, which prevents that liquid or paste filled in can be manipulated or that some other liquid or paste than the one filled in originally can be employed.

The drawings show an injector for dispensing a liquid or pasty drug. However, the invention is also applicable to an applicator for dispensing a liquid or pasty drug.

The invention claimed is:

1. An injector or applicator for dispensing a liquid or pasty drug, comprising
    a housing portion (1),
    a piston body (2), and
    a closing cap (3) with a cap portion (10) for closing the opening (8) of the injector or applicator and connecting portion (9) for connecting the closing cap (3) with the injector or applicator,
    the cap portion (10) and the connecting portion (9) being releasably connected by a tear edge (19), wherein
    the housing portion (1) has an undercut (18) formed by a step fixedly mounted upon an internal surface thereof and facing an interior of the housing (1) and defining an inner diameter smaller than an inner diameter of a remainder of the housing (1) and the piston body (2) has a protrusion,
    such that the piston body (2) is free to move within the housing (1) but when the piston body (2) is retracted from within the housing (1) to an extent where the protrusion contacts the step (18), the protrusion is retained by the step (18) and prevented from being detached from the housing (1), and
    the connecting portion (9) comprises a circumferential bead (11) and housing portion (1) comprises a corresponding groove (12) arranged and configured for engaging the bead (11).

2. The injector or applicator according to claim 1, wherein the piston body (2) is made of one piece.

3. The injector or applicator according to claim 1, wherein the piston body (2) comprises a plunger (15) and a piston (16) which is releasably connected with the plunger (15).

4. The injector or applicator according to claim 1, wherein the plunger (15) and the piston (16) are connected with each other by a sealing tape and/or by a predetermined breaking point.

5. The injector or applicator according to claim 1, wherein the cap portion (10) has a sealing pin (13) protruding from an inside upper terminal region of cap portion (10),
    and the housing portion (1) has a protruding tip (5) through which the opening (8) extends and is arranged to engage the sealing pin (3).

6. The injector or applicator according to claim 1, wherein the bead (11) is configured and arranged to frictionally connect with and be retained in the groove (12) which is has a substantially U-shaped cross-section with a radially outer leg of the U-shaped cross-section extending linearly in an upward direction and a radially inner leg of the U-shaped cross-section including a bevel extending towards a middle of the groove (12).

7. An injector or applicator for dispensing a liquid or pasty drug, comprising
    a housing portion (1),
    a piston body (2), and
    a closing cap (3) with a cap portion (10) for closing the opening (8) of the injector or applicator and connecting portion (9) for connecting the closing cap (3) with the injector or applicator,
    the cap portion (10) and the connecting portion (9) being releasably connected by a tear edge (19), wherein
    the housing portion (1) has an undercut (18) formed by a step fixedly mounted upon an internal surface thereof and facing an interior of the housing (1) and defining an inner diameter smaller than an inner diameter of a remainder of the housing (1) and the piston body (2) has a protrusion,
    such that the piston body (2) is free to move within the housing (1) but when the piston body (2) is retracted from within the housing (1) to an extent where the protrusion contacts the step (18), the protrusion is retained by the step (18) and prevented from being detached from the housing (1),
    the connecting portion (9) comprises a circumferential bead (11) and housing portion (1) comprises a corresponding groove (12) arranged and configured for engaging the bead (11),
    the bead (11) is configured and arranged to frictionally connect with and be retained in the groove (12) which is has a substantially U-shaped cross-section with a radially outer leg of the U-shaped cross-section extending linearly in an upward direction and a radially inner leg of the U-shaped cross-section including a bevel extending towards a middle of the groove (12), and
    the bevel has an angle of 15 to 45° and an adjoining region of the connecting portion (9) extends at an angle of 5 to 15° away from the groove (12).

8. The injector or applicator according to claim 1, wherein the bead (11) is welded in the groove (12) which is has a substantially U-shaped cross-section, with
    a first weld (20) located at a base of the groove (12) and
    a second weld (21) located at an upper end of an outer leg of the U-shaped cross-section.

9. The injector or applicator according to claim 1, wherein the bead (11) is positively connected with the groove (12) which is has a substantially U-shaped cross-section with a radially outer leg of the U-shaped cross-section extending linearly in an upward direction and a radially inner leg of the U-shaped cross-section including a bevel extending towards a middle of the groove (12).

10. An injector or applicator for dispensing a liquid or pasty drug, comprising
    a housing portion (1),
    a piston body (2), and
    a closing cap (3) with a cap portion (10) for closing the opening (8) of the injector or applicator and connecting portion (9) for connecting the closing cap (3) with the injector or applicator,
    the cap portion (10) and the connecting portion (9) being releasably connected by a tear edge (19), wherein
    the housing portion (1) has an undercut (18) formed by a step fixedly mounted upon an internal surface thereof and facing an interior of the housing (1) and defining an inner diameter smaller than an inner diameter of a remainder of the housing (1) and the piston body (2) has a protrusion, such that the piston body (2) is free to move within the housing (1) but when the piston body (2) is retracted from within the housing (1) to an extent where the protrusion contacts the step (18), the protrusion is retained by the step (18) and prevented from being detached from the housing (1), the connecting portion (9) comprises a circumferential bead (11) and housing portion (1) comprises a corresponding groove (12) arranged and configured for engaging the bead (11), the bead (11) is positively connected with the groove (12) which is has a substantially U-shaped cross-section with a radially outer leg of the U-shaped cross-section extending linearly in an upward direction and a radially inner leg of the U-shaped cross-section including a bevel extending towards a middle of the groove (12) and the bevel has an angle of about 90°.

11. An injector or applicator for dispensing a liquid or pasty drug, comprising a housing portion (1), a piston body (2), and a closing cap (3) with a cap portion (10) for closing the opening (8) of the injector or applicator and connecting portion (9) for connecting the closing cap (3) with the injector or applicator, the cap portion (10) and the connecting portion (9) being releasably connected by a tear edge (19), wherein the housing portion (1) has an undercut (18) formed by a step fixedly mounted upon an internal surface thereof and facing an interior of the housing (1) and defining an inner diameter smaller than an inner diameter of a remainder of the housing (1) and the Piston body (2) has a protrusion, such that the piston body (2) is free to move within the housing (1) but when the piston body (2) is retracted from within the housing (1) to an extent where the protrusion contacts the step (18), the protrusion is retained by the step (18) and prevented from being detached from the housing (1), and the tear edge (19) is formed by a radially-extending circumferential ring portion of small cross-section connecting an upper terminal region of the connecting portion (9) with a lower terminal region of the cap portion (10), the tear edge (19) extending in a radial direction with an outer profile edge (22) of the cap portion (10) aligned radially-inwardly of an inner profile edge (23) of the connecting portion (9) and a resulting offset (a) being bridged by the laterally-extending tear edge (19).

12. An injector or applicator for dispensing a liquid or pasty drug, comprising a housing portion (1), a piston body (2), and a closing cap (3) with a cap portion (10) for closing the opening (8) of the injector or applicator and connecting portion (9) for connecting the closing cap (3) with the injector or applicator, the cap portion (10) and the connecting portion (9) being releasably connected by a tear edge (19), wherein the housing portion (1) has an undercut (18) formed by a step fixedly mounted upon an internal surface thereof and facing an interior of the housing (1) and defining an inner diameter smaller than an inner diameter of a remainder of the housing (1) and the piston body (2) has a protrusion, such that the piston body (2) is free to move within the housing (1) but when the piston body (2) is retracted from within the housing (1) to an extent where the protrusion contacts the step (18), the protrusion is retained by the step (18) and prevented from being detached from the housing (1), the piston body (2) comprises a plunger (15) and a piston (16) which is releasably connected with the plunger (15), and the plunger (15) and piston (16) are connected with each other by a slight frictional connection, with the plunger (15) having an elevation (17) at a front end thereof and the piston (16) having a complementary depression on a back side thereof.

13. The injector or applicator according to claim 12, wherein the connecting portion (9) has a clamping portion.

14. An injector or applicator for dispensing a liquid or pasty drug, comprising a housing portion (1), a piston body (2), and a closing cap (3) with a cap portion (10) for closing the opening (8) of the injector or applicator and connecting portion (9) for connecting the closing cap (3) with the injector or applicator, the cap portion (10) and the connecting portion (9) being releasably connected by a tear edge (19), wherein the housing portion (1) has an undercut (18) formed by a step fixedly mounted upon an internal surface thereof and facing an interior of the housing (1) and defining an inner diameter smaller than an inner diameter of a remainder of the housing (1) and the piston body (2) has a protrusion, such that the piston body (2) is free to move within the housing (1) but when the piston body (2) is retracted from within the housing (1) to an extent where the protrusion contacts the step (18), the protrusion is retained by the step (18) and prevented from being detached from the housing (1), and the tear edge (19) is formed by a radially-extending, continuous circumferential ring portion of small cross-section.

15. An injector or applicator for dispensing a liquid or pasty drug, comprising a housing portion (1), a piston body (2), and a closing cap (3) with a cap portion (10) for closing the opening (8) of the injector or applicator and connecting portion (9) for connecting the closing cap (3) with the injector or applicator, the cap portion (10) and the connecting portion (9) being releasably connected by a tear edge (19), wherein the housing portion (1) has an undercut (18) formed by a step fixedly mounted upon an internal surface thereof and facing an interior of the housing (1) and defining an inner diameter smaller than an inner diameter of a remainder of the housing (1) and the piston body (2) has a protrusion, such that the piston body (2) is free to move within the housing (1) but when the piston body (2) is retracted from within the housing (1) to an extent where the protrusion contacts the step (18), the protrusion is retained by the step (18) and prevented from being detached from the housing (1), and additionally comprising a tapering tip (5) integrally formed with the housing (1) and having a channel (6) extending therethrough and communicating with the opening (8) and a larger internal cavity (7) within the housing (1).

16. An injector or applicator for dispensing a liquid or pasty drug, comprising
- a housing portion (1),
- a piston body (2), and
- a closing cap (3) with a cap portion (10) for closing the opening (8) of the injector or applicator and connecting portion (9) for connecting the closing cap (3) with the injector or applicator,
- the cap portion (10) and the connecting portion (9) being releasably connected by a tear edge (19), wherein
- the housing portion (1) has an undercut (18) formed by a step fixedly mounted upon an internal surface thereof and facing an interior of the housing (1) and defining an inner diameter smaller than an inner diameter of a remainder of the housing (1) and the piston body (2) has a protrusion,
- such that the piston body (2) is free to move within the housing (1) but when the piston body (2) is retracted from within the housing (1) to an extent where the protrusion contacts the step (18), the protrusion is retained by the step (18) and prevented from being detached from the housing (1), and
- the step (18) is integrally-formed along the internal surface of the housing (1) having two distinct internal diameters of different size, with a larger of the two diameters positioned between the step (18) and opening (8).

* * * * *